United States Patent [19]

Lyle, Jr. et al.

[11] Patent Number: 4,948,912

[45] Date of Patent: Aug. 14, 1990

[54] ALKYLATING AGENTS AND METHOD OF USE THEREOF

[75] Inventors: Robert E. Lyle, Jr.; Donald J. Mangold; Nollie F. Swynnerton, all of San Antonio, Tex.

[73] Assignee: Southwest Research Institute, San Antonio, Tex.

[21] Appl. No.: 904,884

[22] Filed: Sep. 8, 1986

[51] Int. Cl.$^5$ .............................................. C07C 69/63
[52] U.S. Cl. .................................... 560/227; 560/20; 560/112; 560/230; 546/266
[58] Field of Search ................................ 560/230, 227

[56] References Cited

U.S. PATENT DOCUMENTS 2,732,303 1/1956 Morgan .............................. 560/230

FOREIGN PATENT DOCUMENTS 603966 8/1960 Canada ................................ 560/230
910599 3/1982 U.S.S.R. .............................. 560/227

Primary Examiner—Paul J. Killos

Attorney, Agent, or Firm—Sigalos, Levine & Montgomery

[57] ABSTRACT

The present invention comprises a haloacetoxyalkyl ether having the formula:

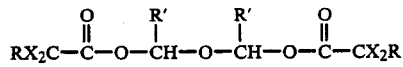

wherein R is H or a $C_1$–$C_4$ substituted or unsubstituted alkyl group, R' is H or a $C_1$–$C_3$ group, and X is chlorine or fluorine; aroyloxymethyl ethers having the formula:

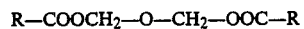

wherein the R is p-$NO_2C_6H_4$, halogen substituted $C_6H_4$, or other aromatics; the method of making such ethers and monoquaternary salts; and the method of alkylating amines, pyridines, or acetals or pyridine derivatives with such ethers to form quaternary ammonium salts; particularly HI-6, HGG-12, Toxogonin, and SAS-128.

8 Claims, No Drawings

ALKYLATING AGENTS AND METHOD OF USE THEREOF

This invention was made under United States Government Contract No. DAMD17-82-C2061 and the United States Government has a nonexclusive, nontransferable, irrevocable, paid-up license to practice, or have practiced for or on behalf of the United States, this invention throughout the world.

BACKGROUND OF THE INVENTION

Quaternary ammonium salts such as HI-6, HGG-12, SAD-128, and Toxogonin are dephosphorylating compounds which are used for the treatment of persons exposed to cholinesterase inhibitors. The reversal of the inhibition of acetyl cholinesterase by phosphorylating agents has also been achieved by treatment with pyridinium aldoxime salts. However, the bis-quaternary salts HI-6, HGG-12, SAD-128, and Toxogonin have been shown to be more effective than the mono-salts.

At the present time, the synthesis of these bisquaternary salts involves a carcinogenic and toxic alkylating agent, bischloromethyl ether ($ClCH_2OCH_2Cl$) as an intermediate reactant. Efforts to form the desired salts without using toxic bischloromethyl ether as the alkylating agent have included the attempted use of the bisacetoxymethyl ether. However, such has not proven useful as an alkylating agent.

In brief, it has not been possible heretofore to effectively alkylate amine derivatives to form such bis-quaternary compounds without the use of toxic alkylating agents.

SUMMARY OF THE INVENTION

The present invention overcomes the problems of the prior art by providing for novel non-toxic and nonmutagenic intermediates as alkylating agents where the leaving group in the alkylating step is a carboxylate moiety.

Briefly stated, the present invention comprises a trihaloacyloxyalkyl ether having the formula: substituted haloacetoxyalkyl ether having the formula:

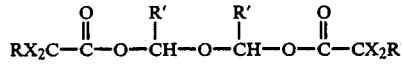

wherein R is X or a $C_1$ to $C_4$ substituted or unsubstituted alkyl group, R' is H or a $C_1$-$C_3$ alkyl group, and X is chlorine or fluorine. The invention also comprises the aroyloxyalkyl ethers having the formula:

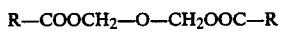

wherein the R is p-$NO_2C_6H_4$, halogen substituted $C_6H_4$, or other like aromatics. The invention further comprises the method of making such ethers and certain monoquaternary salts and the method of alkylating amines, pyridines, or acetals or pyridine derivatives with such ethers to form quaternary ammonium salts; particularly HI-6, HGG-12, SAD-128, and Toxogonin utilizing an iodide catalyst.

DETAILED DESCRIPTION

As to the haloacetoxyalkyl ethers, their preparation will be discussed with reference to preparing bis-trifluoroacetoxymethyl ether, the preferred alkylating agent. For such ether, trifluoroacetic anhydride is reacted with trioxane using sulfuric acid as a catalyst according to the following reaction:

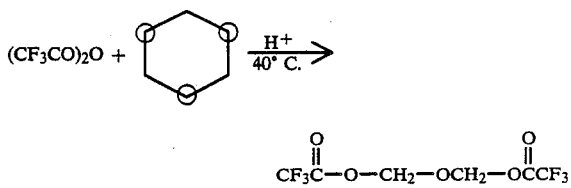

This procedure gives greater than 70% yield of the trifluoroacetoxymethyl ether. Likewise, trichloroacetic anhydride is reacted with trioxane and sulfuric acid to form bistrichloroacetoxymethyl ether.

It will be understood that the corresponding propoxy and butoxy ethers can be formed utilizing, correspondingly, polyfluoropropionic anhydride, or polychloropropionic anhydride, or polyfluorobutyric anhydride, or polychlorobutyric anhydride for the trifluoroacetic anhydride or trichloroacetic anhydride. In like manner, one can use substituted trioxane to obtain the ethyl, propyl, butyl, and pentylethers.

The bis-trifluoroacetoxymethyl ether can be formed by reacting the trifluoroacetic anhydride with trioxane in an acid catalyzed reaction, utilizing such acidic compounds as sulfuric acid as the catalyst. A typical reaction is carried out at 40° C. to 60° C. in the presence of this catalyst at a time sufficient to complete the reaction.

Further, aroyloxymethyl ether compounds of the following formula can be utilized as alkylating agents:

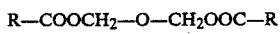

wherein the R is p-$NO_2C_6H_4$, halogen substituted $C_6H_4$, or other like aromatics. More specifically the preparation of the aroyloxymethyl ether compounds will be discussed with reference to preparing bis-2,6-difluorobenzoyloxymethyl ether, bis-2,4-dichlorobenzoyloxymethyl ether, and bis-p-nitrobenzoyloxymethyl ether. Bis-2,6-difluorobenzoyloxymethyl ether is formed by reacting 2,6-difluorobenzoic anhydride with trioxane and sulfuric acid to give bis-2,6-difluorobenzoyloxymethyl ether in 68% yield. Likewise, 2,4-dichlorobenzoic anhydride is reacted with trioxane to yield bis-2,4-dichlorobenzoyloxymethyl ether. Bis-p-nitrobenzoyloxymethyl ether is formed by reacting p-nitronitrobenzoic anhydride with trioxane and sulfuric acid. These alkylating agents formed can then react with compounds, particularly with amines, pyridines or acetals of pyridine derivatives to form the valued bis-quaternary salts. Specifically, bis-trifluoroacetoxymethyl ether is reacted with 3-benzoylpyridine. The initial reaction of bistrifluoroacetoxymethyl ether with 3-benzoylpyridine is carried out at 40° C. to 60° C. The preparation of the bis-quaternary salts is illustrated by the following two-step reaction:

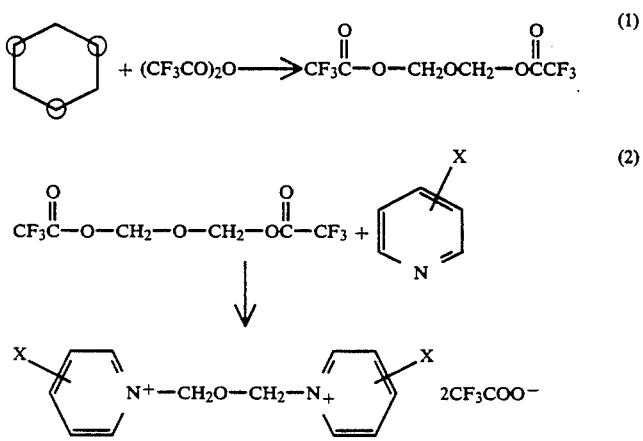

The bis-trifluoroacetoxymethyl ether or alkylating agent can be reacted with an appropriate amine or pyridine derivative to from the valued quaternary salts, such as HI-6, HCG-12, or Toxogonin. The structures of these end-products are illustrated as follows:

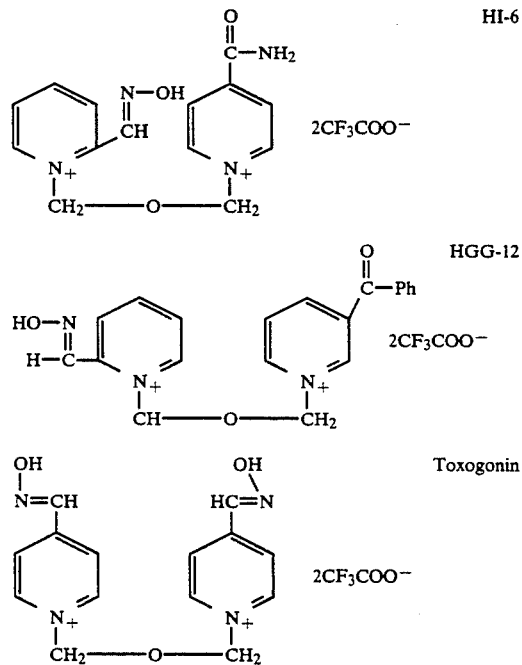

The results showed that the bis-trifluoroacetoxymethyl ether would alkylate pyridine, 3-benzoylpyridine, and 4-t-butylpyridine to give the bis-quaternary salts; however, pyridine-2-aldoxime, pyridine-4-aldoxime, pyridine-2-aldehyde, and pyridine-4-aldehyde gave anomalous reactions when reacted with the alkylating ethers.

It has also been found that if it is desired to prepare bis-quaternary salts with different terminal troups, it is best to utilize mono-quaternary salts of the formula:

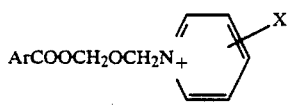

wherein Ar is selected from $2,4\text{-}Cl_2C_6H_3$ or $2,6\text{-}F_2C_6H_3$ and X is hydrogen or 3-PhCO.

These salts are formed by reacting pyridine or 3-benzoylpyridine with bis(2,4-dichlorobenzoyloxymethyl) ether or bis(2,6-difluorobenzoyloxymethyl) ether. Such reaction is effected by heating the mixture of reactants at the fusion temperature; preferably under agitation. The reaction time will vary widely dependent upon the particular reactants, but essential completion of the reaction can be determined by a thickening or solidification of the reaction mixture. Catalysts such as sodium iodide are also preferably used.

Such salts, when reacted with pyridine and 4-t-butylpyridine and the like, using a conventional appropriate solvent if both reactants are solids, and in the presence of a catalyst such as sodium iodide, produce the bis-quaternary salts. More specifically, the monoquaternary salt of 3-benzoylpyridine can be reacted with pyridine or 4-t-butylpyridine to give the bis-quaternary salts, including SAD-128.

The ethylene glycol acetal of 4-pyridinealdehyde, also known as 4-(1,3-dioxolan-2-yl)-pyridine, was reacted with bis-trifluoroacetoxymethyl ether using the following starting materials:
(1) 1 mole ester: 2 moles acetal in tetrahydrofuran (THF) at reflux
(2) 1 mole ester: 2 moles acetal with no solvent at 45° C.
(3) 1 mole ester: 2 moles acetal with no solvent with NaI added The product was worked up with ether and the residue was dissolved in chloroform. Addition of ether caused a precipitation which on redissolution and reprecipitation was studied by NMR and appeared to be that of the desired bis-quaternary salt. Reaction with hydroxylamine hydrochloride gave Toxogonin.

Alkylation of the bis-trifluoroacetoxymethyl ether with amines, pyridines, or acetals of pyridine derivatives may be enhanced by the addition of NaI or NH$_4$I. Specifically, the catalytic effect of NaI in the alkylation of 4-(1,3-dioxolan-2-yl)-pyridine with bistrifluoroacetoxymethyl ether is demonstrated. The preferred ammonium salt utilized is tetrabutylammonium iodide.

The invention will be further illustrated in conjunction with the following examples, which are set forth for purposes of illustration only and not by way of limitation.

EXAMPLE 1

A solution of 19.8 g (0.22 m) of trioxane and 0.10 mL of sulfuric acid in 208 g (1.0 m) of trifluoroacetic anhydride was heated at 40° C. for 4 days. The reaction mixture was distilled at 20 mm using an 8" Vigreaux column to give results shown in Table 1.

TABLE 1

| Fraction No. | Boiling Range, °C. | Pressure, mm HG | Wt, g | \multicolumn{4}{c}{$CF_3COO(CH_2O)_xCOCF_3$ Product Distribution mol percent[a] x =} | | | |
|---|---|---|---|---|---|---|---|
| | | | | 1 | 2 | 3 | 4 |
| 1 | 18–47 | 10 | 2.32 | 69 | 21 | 7 | 3 |
| 2 | 47–48 | 2.2 | 20.38 | 0 | 100 | 0 | 0 |
| 3 | 48–57 | 0.5 | 2.39 | 0 | 76 | 22 | 2 |
| 4 | 57 | 0.5 | 8.63 | 0 | 19 | 76 | 5 |
| Pot Residue | | | 0.28 | | | | |
| Accountability - 91%[b] | | | | | | | |

[a]Determined by NMR
[b]Some solid remained on walls of distillation apparatus and it is likely that not all of the volatiles were condensed.

The structure of bis-trifluoroacetoxymethyl ether was confirmed for fraction 2 by NMR spectra.

EXAMPLE 2

A mixture of 102.7 g of trifluoroacetic anhydride and 9.9 g of trioxane was treated with 0.2 mL of sulfuric acid. After 30 hours of heating the NMR spectrum of an aliquot showed 74.5% of the desired bistrifluoroacetoxymethyl ether and further heating led to decomposition. At 47 hours only 68.6% of the reaction mixture was the desired ester. On distillation of the reaction mixture further equilibration occurred to give finally an 85% yield of the ester.

EXAMPLE 3

A mixture of 30.9 g trichloroacetic anhydride, 2.25 g s-trioxane and 65 μL concentrated sulfuric acid was heated in an oil bath at 50° C. for 24 hrs. The mixture was distilled to yield 11.23 g (81%) bis-trichloroacetyloxymethyl ether bp 127°–129° C./0.10–0.12 mm.

EXAMPLE 4

A suspension of 9.49 g of p-nitrobenzoic anhydride, 0.90 g of trioxane and two drops of sulfuric acid in 50 mL of benzene was heated under reflux for 10 days. Seven additional portions of trioxane were added at one-day intervals. The cooled reaction mixture was filtered to give 7.2 g of recovered anhydride as residue and 3.32 g of a mixture of anhydride and product on evaporation of the solvent. The latter mixture was treated with chloroform and filtered. The insoluble material was largely anhydride and on evaporation of the filtrate 1.2 g of impure product was obtained. The product was separated from the anhydride by dissolving in DMSO and precipitating by adding to 10% sodium carbonate. The solid which precipitated was recrystallized from chloroform-petroleum ether to give 0.31 g of bis-p-nitrobenzoyloxymethyl ether.

EXAMPLE 5

A solution of 2 g of 2,6-difluorobenzoic anhydride, 0.30 g of trioxane, and 1 drop of sulfuric acid in 5 mL of methylene chloride was allowed to stand at room temperature for four days. The mixture was diluted to 40 mL with methylene chloride. The solution was extracted with 5% sodium carbonate solution and water, dried over magnesium sulfate, and concentrated to yield 2 g of a pale yellow oil which crystallized on standing. The residue was recrystallized twice from ether to yield 1.02 g (68%) of bis-2,6-difluorobenzoyloxymethyl ether, mp 52°–53° C.

EXAMPLE 6

The reaction was run as above with 1.73 g of 2,4-dichlorobenzoic anhydride and 0.21 g of trioxane. After 18 hours the reaction was stopped and the product isolated as above to give 1.56 g of a mixture of the bis-2,4-dichlorobenzoyloxy methane and bis-2,4-dichlorobenzoyloxymethyl ether. The ether obtained by fractional crystallization from chloroform-hexane gave 0.28 g (19%) of needles, mp 80.5°–81.5° C.

EXAMPLE 7

A mixture of 0.74 g (4 mmol) of 3-benzoylpyridine with 0.54 g (2 mmol) of bis-trifluoroacetoxymethyl ether was warmed and at about 42° C. a solution resulted. After 2 hours the dark mixture solidified. The mass was cooled, transferred with chloroform to an Erlenmeyer flask triturated with 25 mL of chloroform with warming. Filtration gave 0.75 g (59%) of the bis-quaternary salt. The solid was purified by washing with chloroform.

EXAMPLE 8

A solution of 1.0 g (5.5 mmol) of 3-benzoylpyridine and 1.47 g (5.5 mmol) of bis-trifluoroacetoxymethyl ether (equimolar ratios) in 5 mL of diethyl ether was allowed to stand at room temperature. After standing two days the ether supernatant layer was decanted from the solid which precipitated. The solid was 0.26 g of the bis-quaternary salt.

EXAMPLE 9

A solution of 5 g of 2-(4'-pyridyl)-1,3-dioxolane in 4.13 g of bis-trifluoroacetyloxymethyl ether and 0.5 g of sodium iodide was allowed to stand overnight. The reaction mixture was washed with ether, and the ether insoluble oil treated with 8.0 g of hydroxylamine hydrochloride and hydrochloric acid. The solvent was removed by evaporation and the residual salt converted to the chloride by ion exchange to give the valued Toxogonin, mp 205°–206° C.

EXAMPLE 10

A solution of 25 g of 4-t-butylpyridine and 27.8 g of sodium iodide in 25 g of bis-trifluoroacetoxymethyl ether was cooled during preparation and slowly warmed to room temperature. Acetone was added and the solid collected. Recrystallation from ethanol gave 30.9 g of the bis-quaternary salt SAD-128 diiodide, mp 252°–256° C. The chloride form was obtained by ion exchange on a Dowex column to give 17.7 g of SAD-128 dichloride, mp 228°–231° C.

EXAMPLE 11

A 3-neck flask equipped with nitrogen inlet and outlet tubes and a Hirschberg stirrer was charged with 43.1 g (0.236 mol) of 3-benzoylpyridine and 33 g (0.079 mol) of bis-2,4-dichlorobenzoyloxymethyl ether. The solids were melted via a steam-bath, and another 33 g of the ether was added and melted. A final 33 g of the ether was added along with 35.35 g (0.236 mol) of NaI, and the mixture was placed in a 65° C. oil bath. The mixture was vigorously stirred with heating for 3 days. The thickened orange syrup was triturated with 1400 mL Et$_2$O. The Et$_2$O, when evaporated, contained 71.0 g (71%) of the unreacted bis-ether and 28 g (65%) of unreacted 3-benzoylpyridine. The Et$_2$O insoluble residue was slurried in 150 mL acetone and precipitated with 1400 mL Et$_2$O. The acetone/Et$_2$O was decanted from the oil and the insoluble oil was dried under reduced pressure. The dried oil was slurried in 150 mL of acetone and precipitated with 1400 mL of Et$_2$O to give a solid. This yellow solid was separated by filtration and washed with two 250 mL portions of acetone to give 3.4 g (12% corrected yield) of bis salt, mp 210°–212° C. The acetone extracts were combined and evaporated to yield 26.53 g (71% corrected yield) of monosalt:

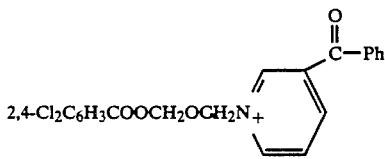

mp 103°–107° C. The crude monosalt was washed with Et$_2$O and separated by filtration to yield 25.9 g (70% corrected yield) of the monosalt (orange solid), mp 105°–107° C.

EXAMPLE 12

The apparatus of Example 11 was utilized to react 1.5 g (4.0 mmol) bis-2,6-difluorobenzoyloxymethyl ether, 1.02 g (5.58 mmol) 3-benzoylpyridine, and 0.84 g of sodium iodide with stirring at 68°–70° C. for 16 hours. The reaction mixture solidified and was transferred to an Erlenmeyer flask and washed with 100 mL of ether, 20–30 mL water, slurried in 20 mL acetone and precipitated with 100 mL ether. The precipitated solid was extracted with acetone and centrifuged to remove 0.07 g of undissolved bis salt. The acetone was evaporated to yield 0.80 g (30% estimated yield) of crude monosalt:

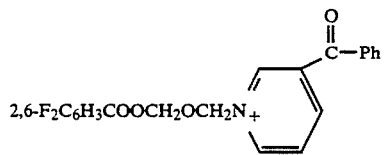

From the ether wash was obtained 2.03 g of a mixture of the ether and 3-benzoylpyridine.

EXAMPLE 13

The apparatus of Example 11 was utilized to react 0.13 g pyridine, 1.43 g of bis-2,4-dichlorobenzoyloxymethyl ether and 0.25 g NaI neat at 80° C. for 30 minutes to give a solid. The solid mixture was washed three times with 50 mL of Et$_2$O and then acetone/Et$_2$O. The NMR spectrum of the insoluble solid from the final wash indicated pyridine monosalt:

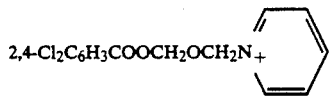

was present in the partial solution in acetone d$_6$. The acetone insolubles were dissolved in DMSO-d$_6$ and $^1$H NMR suggests it was a mixture of bis-salt and starting bisester.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A non-toxic and non-mutagenic haloacetoxyalkyl ether having the formula:

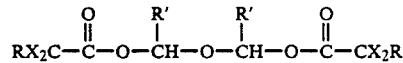

wherein R is X, a C$_1$ to C$_4$ aryl substituted or unsubstituted alkyl group, R' is H or a C$_1$–C$_3$ alkyl group, and X is chlorine or fluorine.

2. A bis-trifluoroacetoxymethyl ether having the formula:

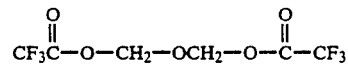

3. A process for the manufacture of the trifluoroacyloxyalkyl ether of claim 1 or 2 comprising reacting trioxane with an acid anhydride in an acid catalyzed reaction for a time and at a temperature sufficient to form the ether.

4. The process of claim 3 wherein the acid anhydride is trifluoroacetic anhydride.

5. The process of claim 3 or 4 wherein the reaction is catalyzed by sulfuric acid at room temperature.

6. In the process for the manufacture of bis-quaternary compounds comprising alkylating an amine, pyridine, acetal, or pyridine derivative, the improvement comprising using as the alkylating agent a haloacetoxyalkyl ether having the formula:

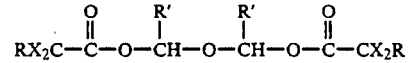

wherein R is X or a C$_1$ to C$_4$ aryl substituted or unsubstituted alkyl group, R' is H or a C$_1$–C$_3$ alkyl group, and X is chlorine or fluorine.

7. The process of claim 6, wherein the alkylating agent is a bis-trifluoroacetoxy methyl ether.

8. The process of claim 6, wherein the alkylating agent is bis-trichloroacetoxymethyl ether.

* * * * *